United States Patent
Okuda et al.

(10) Patent No.: US 9,486,289 B2
(45) Date of Patent: Nov. 8, 2016

(54) APPARATUS FOR SUPPORTING AND FOLLOWING MOVEMENT OF A PART OF PERSON'S BODY

(71) Applicants: DENSO CORPORATION, Kariya, Aichi-pref. (JP); SHINSHU UNIVERSITY, Matsumoto, Nagano-pref. (JP); TOKYO WOMEN'S MEDICAL UNIVERSITY, Tokyo (JP)

(72) Inventors: Hideki Okuda, Nagoya (JP); Kazuhiro Hongo, Matsumoto (JP); Tetsuya Goto, Matsumoto (JP); Yosuke Hara, Matsumoto (JP); Jun Okamoto, Tokyo (JP)

(73) Assignees: DENSO CORPORATION, Kariya (JP); SHINSHU UNIVERSITY, Matsumoto (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 287 days.

(21) Appl. No.: 14/249,472

(22) Filed: Apr. 10, 2014

(65) Prior Publication Data
US 2014/0306086 A1 Oct. 16, 2014

(30) Foreign Application Priority Data

Apr. 11, 2013 (JP) ................................. 2013-083073

(51) Int. Cl.
| | |
|---|---|
| A47F 5/00 | (2006.01) |
| A61B 19/00 | (2006.01) |
| F16M 11/12 | (2006.01) |
| F16M 11/04 | (2006.01) |
| F16M 11/06 | (2006.01) |

(Continued)

(52) U.S. Cl.
CPC ............ *A61B 19/28* (2013.01); *A61B 90/60* (2016.02); *F16M 11/046* (2013.01); *F16M 11/12* (2013.01);

(Continued)

(58) Field of Classification Search
CPC ... A61B 19/28; A61B 2019/266; F16M 11/06; F16M 11/2014; F16M 11/24; F16M 2200/021; F16M 11/046; F16M 11/12; F16M 2200/041
USPC ........ 248/118, 118.1, 118.3, 280.11, 281.11; 297/411.35–411.39
See application file for complete search history.

(56) References Cited

U.S. PATENT DOCUMENTS 2,614,558 A * 10/1952 Lovell ...................... A61F 5/04
248/118
3,390,477 A * 7/1968 Galbraith .............. F41C 33/001
248/118

(Continued)

FOREIGN PATENT DOCUMENTS

| JP | H10-272163 A | 10/1998 |
| JP | 2009-291363 A | 12/2009 |

*Primary Examiner* — Gwendolyn Baxter
(74) *Attorney, Agent, or Firm* — Posz Law Group, PLC

(57) ABSTRACT

An apparatus includes a brace being mounted on a person's body part and having a hard fitting surface. The apparatus also includes a load device, a support, a securing member, a brake, a switch device, and a soft film. The load device has a hard receiving surface receiving the fitting surface of the brace. The support movably supports the load device. The securing member secures the fitting surface to the receiving surface and enables the load device to move and follow movement of the person's body part and the brace against resistance applied from the support. The brake limits movement of the load device. The switch device switches operation modes of the apparatus, at least, between a free mode and a limiting mode. The soft film is arranged between the receiving and fitting surfaces for smooth movement of the person's body part on the load device in the limiting mode.

20 Claims, 14 Drawing Sheets

(51) Int. Cl.
*F16M 11/24* (2006.01)
*F16M 11/20* (2006.01)

(52) U.S. Cl.
CPC ......... *A61B 2090/508* (2016.02); *F16M 11/06* (2013.01); *F16M 11/2014* (2013.01); *F16M 11/24* (2013.01); *F16M 2200/021* (2013.01); *F16M 2200/041* (2013.01)

(56) References Cited

U.S. PATENT DOCUMENTS

| | | | | |
|---|---|---|---|---|
| 3,698,791 A | * | 10/1972 | Walchle | G02B 7/001 359/510 |
| 5,927,815 A | | 7/1999 | Nakamura et al. | |
| 7,337,483 B2 | * | 3/2008 | Boucher | A61G 13/12 5/621 |
| 9,125,652 B2 | * | 9/2015 | Federle | A61B 19/081 |
| 2005/0012376 A1 | * | 1/2005 | Siminovitch | A47C 7/54 297/411.35 |
| 2005/0029413 A1 | * | 2/2005 | Bryant | F41B 5/148 248/118 |
| 2006/0186280 A1 | * | 8/2006 | Thompson | A61F 4/00 248/118 |
| 2014/0014804 A1 | * | 1/2014 | Okuda | A61B 19/28 248/550 |
| 2015/0257843 A1 | * | 9/2015 | Nakamura | F16M 13/022 248/118 |

* cited by examiner

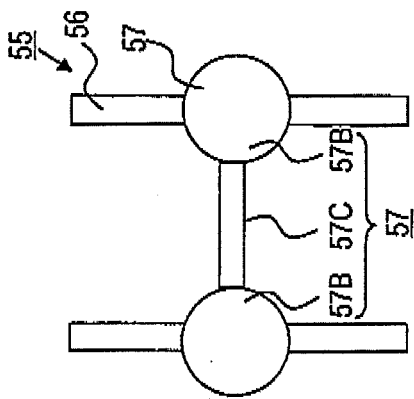
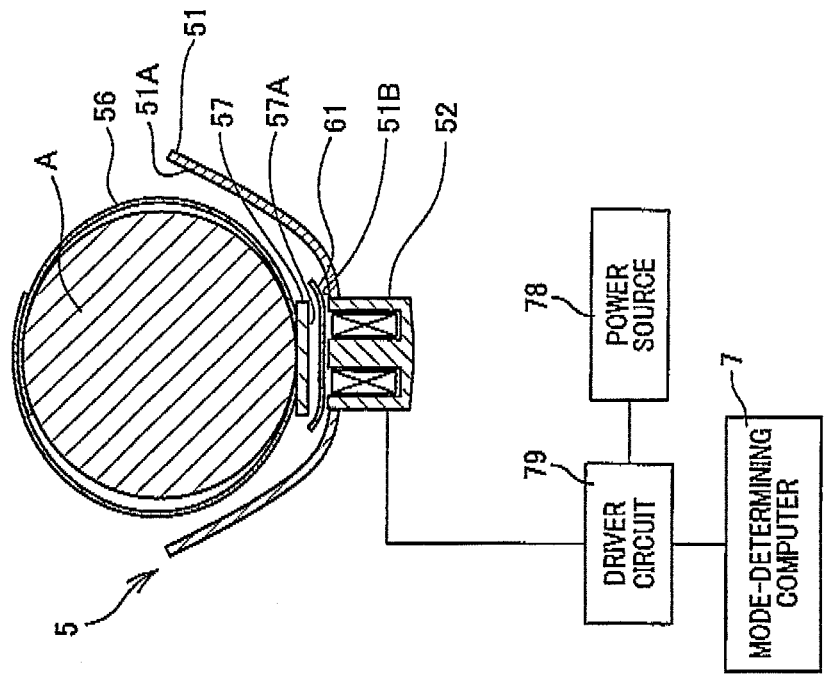

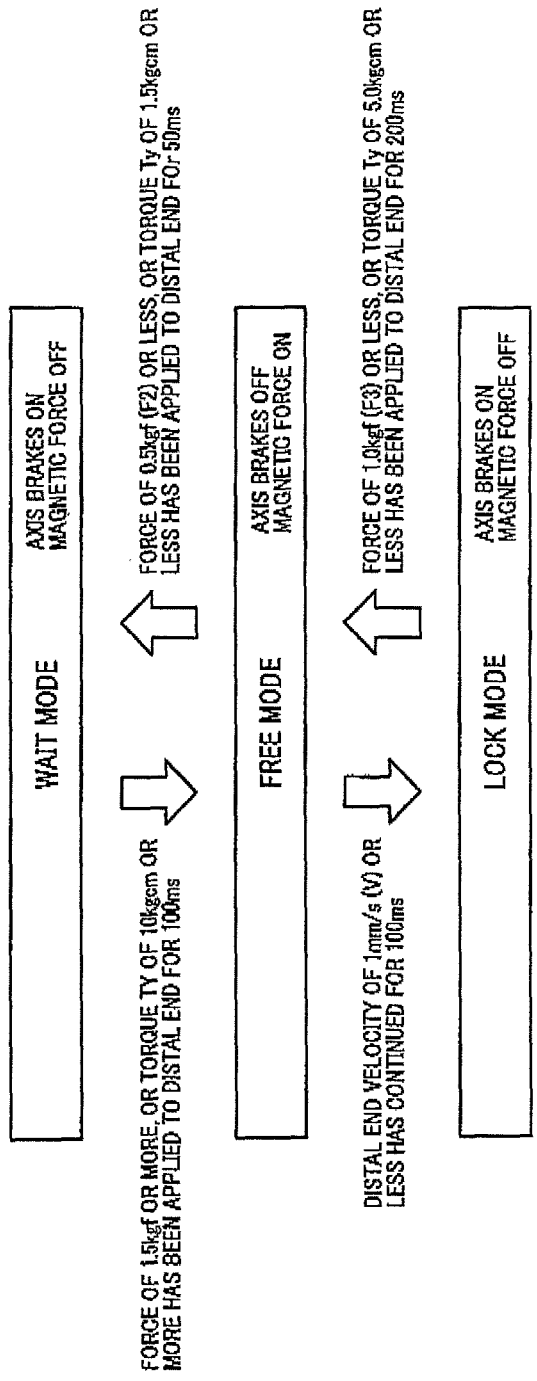

APPARATUS FOR SUPPORTING AND FOLLOWING MOVEMENT OF A PART OF PERSON'S BODY

CROSS-REFERENCE TO RELATED APPLICATION

This application is based on and claims the benefit of priority from earlier Japanese Patent Application No. 2013-083073 filed Apr. 11, 2013, the description of which is incorporated herein by reference.

BACKGROUND

1. Technical Field

The present invention relates to an apparatus for supporting and following the movement of a part of a person's body, and in particular, to an apparatus for supporting and following the movement of a part of a person's body, which is provided with a load device on which a part of a person's body is to be placed (i.e., loaded), the apparatus including an operating mode for permitting the load device to follow the movement of a part of a person's body and an operating mode for limiting the movement of the load device.

2. Related Art

A work that requires delicate hand operation, such as a neurosurgical operation, may involve the use of an apparatus for supporting and following the movement of a part of a person's body, to use the apparatus to support an arm of the worker. In such an apparatus, when the worker wishes to move the worker's arm, a support for supporting the arm is required to follow the movement of the arm. Also, when the worker wishes to lock the worker's arm, the support is required to be locked. For this purpose, JP-A-H10-272163, for example, suggests that a surgeon's arm, for example, be fastened to a support via a belt member, the support being provided at a distal end of a movable articulated holding arm. Thus, the support is permitted to follow the movement of the surgeon's arm. Further, when a foot switch is operated, the articulated holding arm is prohibited from moving to thereby lock the support.

However, in the apparatus disclosed in JP-A-H10-272163, the surgeon has to unfasten the belt member every time the surgeon is required to remove his/her arm from the support to temporarily place a surgical tool, such as tweezers, on a work table or the like, and thus the operability is impaired. In this regard, JP-A-2009-291363 suggests use of an arm rest (corresponding to the support of JP-A-H10-272163) supported by a multijoint arm. Specifically, the multijoint arm is applied with a force so that the arm rest is urged upward to thereby press the arm rest against the surgeon's arm from below. Thus, the arm rest is permitted to follow the movement of the surgeon's arm. In this case, when the movement of the multijoint arm is prohibited to lock the arm rest, the surgeon can easily carry out the surgery while placing his/her arm on the arm rest, or can easily remove his/her arm from the arm rest.

However, in the apparatus disclosed in JP-A-2009-291363, when the arm rest is permitted to move with the movement of the surgeon's arm, the surgeon's arm is constantly pressed upward by the arm rest. Therefore, for example, when the surgeon desires to move his/her arm downward, he/she has to move his/her arm against the pressing force of the arm rest. Thus, the pressing force of the arm rest could prevent the smooth procedure of the surgery. Further, JP-A-2009-291363 suggests detecting the force applied to the arm rest from the surgeon's arm to release braking applied by a brake. However, in this case, the surgeon's arm is required to be prevented from being abruptly pressed by the arm rest immediately after the release.

As a measure against this, the applicants of the present so invention suggest providing a securing member to the base (corresponding to the support of JP-A-H10-272163) which is movably supported by a support that includes a brake and a balancing mechanism to thereby secure the arm of the surgeon. As disclosed in Japanese Patent Application No. 2012-158125 in particular, the applicants further suggest that the operating mode be switched as follows. Specifically, according to this patent application, when the operating mode is switched to free mode, the surgeon's arm is secured to the base by the securing member. Further, in the free mode, the limitation in the movement of the base imposed by the brake is released. Therefore, without the surgeon's necessity of putting so much strength into his/her arm, the base will follow the movement of the surgeon's arm. On the other hand, in a limiting mode, the securing of the surgeon's arm by the securing member is released, while the movement of the base is limited by the brake. Therefore, when the surgeon's arm is moved on the base or removed from the base, the position of the base is retained.

According to the technique of the patent application set forth above, it is true that a part of a person's body, such as an arm, can be freely moved, including removal of a part of a person's body from the base, when the operating mode is limiting mode. However, when a surgeon, for example, wishes to only slightly move his/her arm, with his/her arm being placed on the base, the ease of the movement of his/her arm is still insufficient and there is room for improvement in the easiness. JP-A-2009-291363 suggests that a micromotion mode be provided to such an apparatus to control a powder brake, for example, for little-by-little movement of the base. However, in this case, the number of required actuators or sensors is increased to complicate the configuration and the control of the apparatus.

SUMMARY

It is thus desired to provide an apparatus for supporting and following the movement of a part of a person's body, which includes a limiting mode for releasing the securing of a part of a person's body to a load device, while limiting the movement of the load device, the apparatus having a simple configuration that enables smooth movement of a part of a person's body on the load device in the limiting mode.

The apparatus for supporting and following the movement of a part of a person's body of the present disclosure includes a load device. The load device has a receiving surface on which a fitting surface of a brace mounted on a part of a person's body is placed. The load device also has a securing member that secures the receiving surface to the fitting surface. The load device is movably supported by a support which has at least one joint and is flexed by the joint. With the securing established by the securing member, the load device can move, following the movement of a part of a person's body and the brace against the resistance applied from the support. The apparatus also includes a brake that suppresses the flex in the at least one joint of the support to thereby limit the movement of the load device. The securing established by the securing member is released by mode switching performed as follows by a switching means. Accordingly, a part of a person's body as well as the brace can be easily placed on or removed from the load device.

Specifically, when the switching means switches the operating mode to free mode, the securing member establishes securing and the limitation of the movement of the load device imposed by the brake is released. Accordingly, the load device can follow the movement of a part of a person's body and the brace without the person's necessity of putting so much strength into the part of the person's body.

On the other hand, when the switching means switches the so operating mode to limiting mode, the securing established by the securing member is released and the movement of the load device is limited by the brake. Accordingly, during work, the worker is able to easily place a part of his/her body and the brace on the load device to permit the load device to follow the movement of the part of his/her body, or easily remove the part of his/her body and the brace from the load device. In this case, since a soft film is arranged between the receiving surface and the fitting surface, the sliding resistance acting between the receiving surface and the fitting surface is reduced. Specifically, since a soft film having small shear strength is arranged between a hard receiving surface and a hard fitting surface, the friction coefficient between the receiving surface and the fitting surface is reduced. Therefore, only a slight movement of a part of a person's body and the brace on the load device can cause a smooth movement of the part of the person's body and the brace. The person's arm and the brace placed on the load device are moved without being controlled by actuators or sensors. Accordingly, complication in the configuration or the control of the apparatus is minimized.

The load device may include inclined surfaces that guide the fitting surface of the brace to the receiving surface. In this case, when a part of a person's body is arranged on the load device, the fitting surface slides down along the inclined surfaces and are guided into the receiving surface, ensuring more enhanced controllability.

In the present embodiment, the securing member may include an electromagnet, while the fitting surface of the brace may be mounted with a magnetic member, and the film may be a non-magnetic film. In this case, when the electromagnet is demagnetized to release the securing, the remnant magnetic flux that acts on the magnetic member mounted to the fitting surface is reduced by the non-magnetic film, thereby enhancing the responsiveness. Thus, the part of a person's body and the brace can be more smoothly moved.

BRIEF DESCRIPTION OF THE DRAWINGS

In the accompanying drawings:

FIGS. 3A and 3B are schematic views each illustrating an end arm of the apparatus;

FIG. 15 is a state transition diagram illustrating transition of operating mode according to the control.

DETAILED DESCRIPTION OF THE PREFERRED EMBODIMENTS

Figure 1:
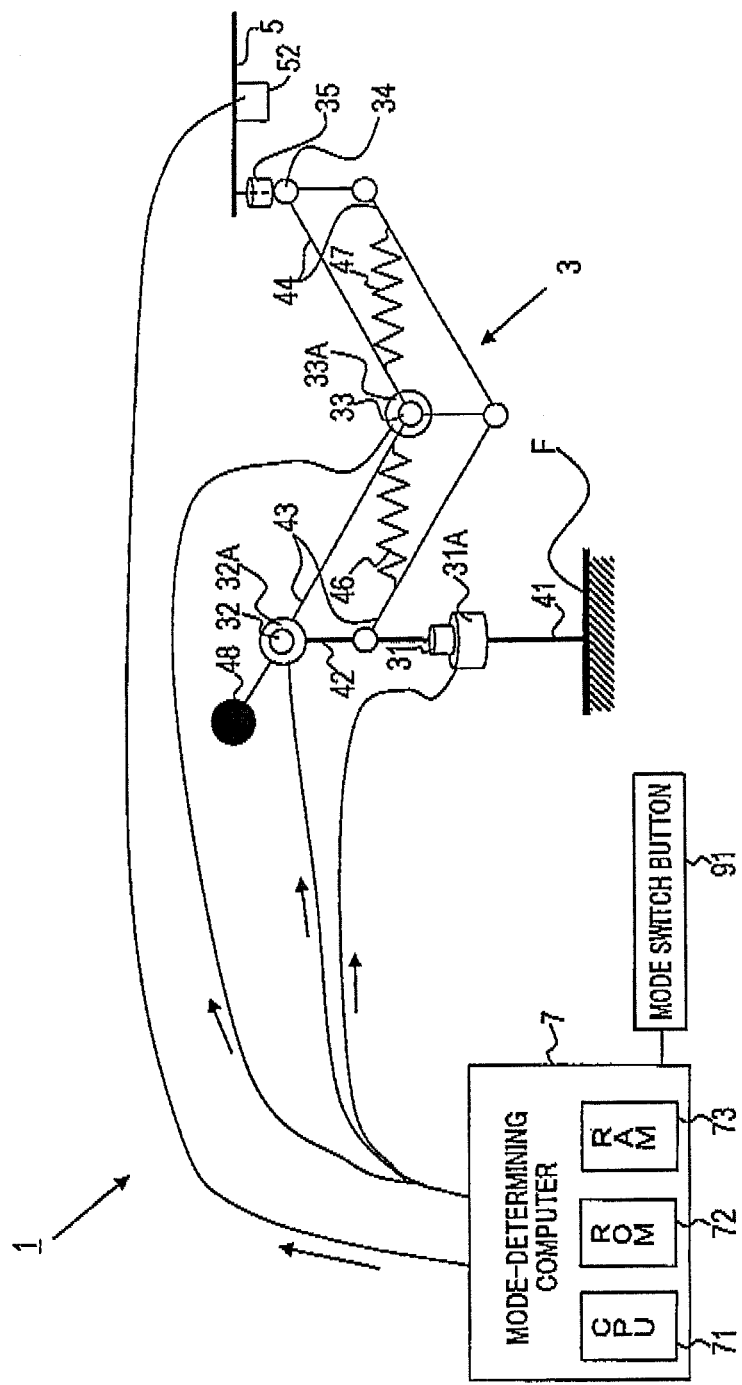
FIG. 1 is a schematic view illustrating an apparatus for supporting and following the movement of a part of a person's body, according to a first embodiment to which the present invention is applied.

With reference to the accompanying drawings, hereinafter are described several embodiments of the present invention. In the following embodiments, the components identical with or similar to each other between the embodiments are given the same reference numerals for the sake of omitting unnecessary explanation.

Each embodiment provided below describes an apparatus for supporting an arm "A" (see FIG. 3) that is a part of a body of a surgeon, as a worker, who carries out a surgery. However, the apparatus for supporting and following the movement of a part of a person's body of the present invention can alternatively be applied such as to operations for manufacturing precision machinery, in which the apparatus may support a hand, a finger, a foot and the like, other than the arm A.

First Embodiment

Referring FIGS. 1 to 5, a first embodiment of the present invention is described.

Figure 2A:
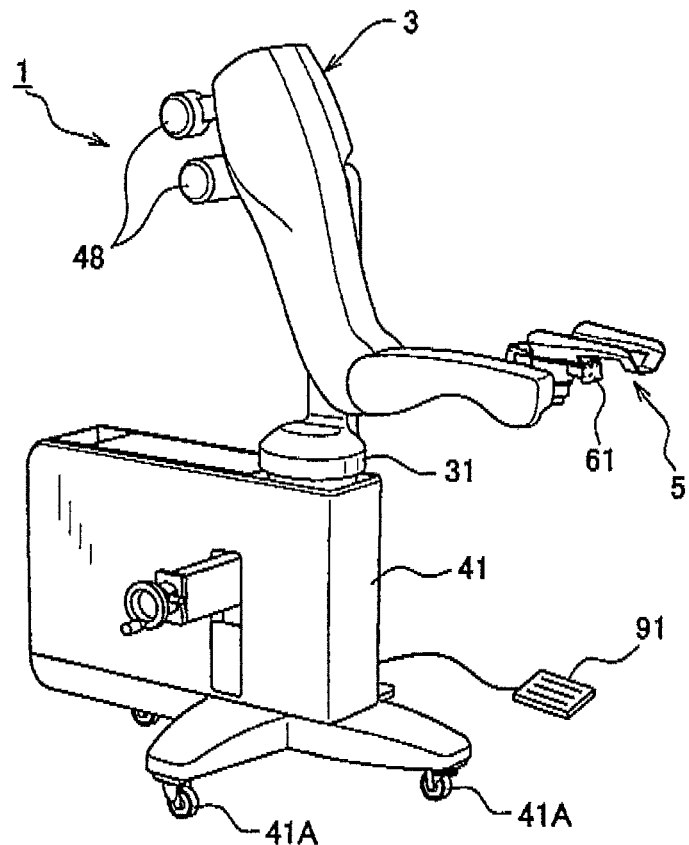
FIGS. 2A and 2B are a perspective views each illustrating the appearance of the apparatus.
Figure 2B:
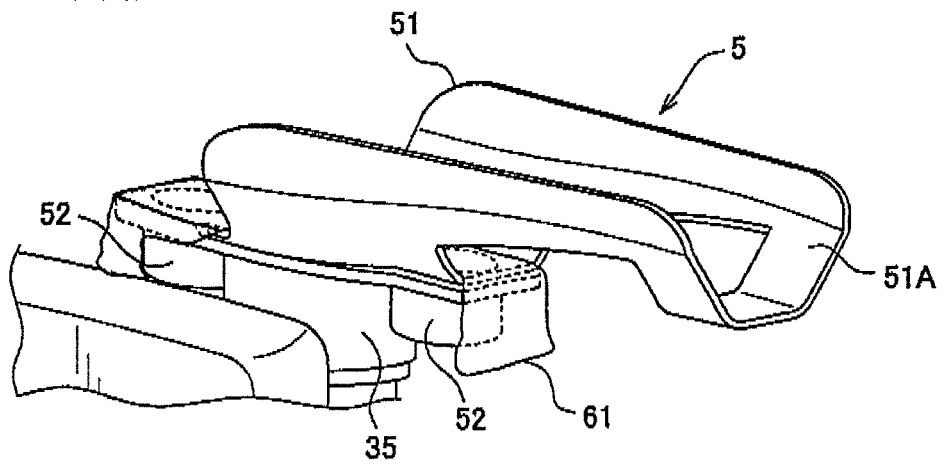

FIG. 1 is a schematic view illustrating an apparatus 1 for supporting and following the movement of a part of a person's body (hereinafter also just referred to as apparatus 1), according to a first embodiment to which the present invention is applied. FIGS. 2A and 2B are perspective views each illustrating an appearance of the apparatus 1. As shown in FIG. 2A, the apparatus 1 includes a multijoint arm 3, an end arm 5 which is mounted to a distal end of the multijoint arm 3 and which functions as a load device (on which a part of a person's body, such as an arm, is to be loaded), and a mode-determining computer 7 which controls the multijoint arm 3 and the end arm 5. When the part of a person's body is an arm, the end arm 5 thus functions as an armrest. The multijoint arm 3 is a movement mechanism that movably supports the end arm 5 in accordance with an external force that acts on the end arm 5. The multijoint arm 3 has five joints 31, 32, 33, 34 and 35 and is configured to possess five degrees of freedom. The joints 31, 32, 33, 34 and 55 are all rotary joints.

The multijoint arm 3 is provided with a support 41 which is fixed to a floor F of a surgery room. The support 41 supports the whole multijoint arm 3 as explained below. Specifically, the support 41 has an upper end to which a shoulder 42 is connected via the joint 31 so as to be rotatable about a vertical axis. Also, the joint 31 is provided with a brake 31A which is an electromagnetic brake that suppresses the rotation of the support 41 and the shoulder 42 in the joint 31.

As shown in FIG. 2A, the support 41 is provided with casters 41A so as to ensure easy movement of the support 41 on the floor F. The casters 41A are provided with respective well-known stoppers (not shown) and accordingly the support 41 can be fixedly located at a desired position on the floor F.

As shown in FIG. 1, the shoulder 42 has an upper end to which an end of a first arm 43 is connected via the joint 32 so as to be pivotally rotatable about a horizontal axis. The first arm 43 is configured as a parallel link mechanism in which both ends of two rods are retained so as to have a given interval therebetween in the vertical direction, with an end of the upper rod being connected to the joint 32. The first arm 43 has the other end to which an end of a so second arm 44, which is configured as a similar parallel link mechanism, is connected via the joint 33 so as to be pivotally rotatable about a horizontal axis. The second arm 44 has the other end to which the end arm 5 (i.e., the armrest) is connected via the joints 34 and 35. The joint 34 is rotatable about a horizontal axis. The joint 35 has a rotational axis perpendicular to that of the joint 34.

Similar to the joint 31, the joints 32 and 33 are provided with brakes 32A and 33A, respectively. Further, springs 46 and 47 are provided between the joint 33 and the first arm 43 and between the joint 33 and the second arm 44, respectively. The first arm 43 is extended, passing through the joint 32, with the extended end being provided with a counter weight 48. The springs 46 and 47 and the counter weight 48 achieve a balance with the force applied to the end arm 5 and the multijoint arm 3 when the surgeon's arm A is placed on the end arm 5.

Specifically, the biasing force applied by the springs 46 and 47 and the counter weight 48 is balanced with the dead weight of the end arm 5 (practically, the armrest) that includes electromagnets 52 (see FIG. 3A), which will be described later, the dead weight of the arm A, the dead weight of a brace 55, which will be described later, and the dead weight of the multijoint arm 3, thereby supporting the end arm 5. The biasing force may ideally be completely balanced with the dead weights. However, taking into account that the surgeon's hands carry out the surgery from above the affected area of a patient, the biasing force is set so as to urge the end arm 5 upward, i.e. in a risk-free direction, with quite a weak force. If the balancing is achieved by the counter weight 48 alone, the springs 46 and 47 may be omitted.

FIGS. 3A and 3B are schematic views each illustrating the end arm 5 of the apparatus 1. As shown in FIGS. 3A and 3B, the end arm 5 includes the brace 55. The brace 55 is configured by a pair of bands 56 that are wound about the arm A, and a magnetic member 57 attached to the bands 56. The magnetic member 57 includes a pair of disc-shaped parts 57B and a rod-shaped part 57C. The disc-shaped parts 57B are directly fixed to the respective bands 56. The rod-shaped part 57C connects the pair of disc-shaped parts 57B to each other. The magnetic member 57 includes fitting surfaces 57A which are located on the other side the arm A. The fitting surfaces 57A are configured to be flush with each other (see FIG. 3B). The brace 55 is mounted on the arm A such that the magnetic member 57 is located under the arm A when the arm A is extended forward.

As shown in FIGS. 2B and 3B, the end arm 5 includes an arm holder 51 and the electromagnets 52. The arm holder 51 is used for placing thereon the arm A that has mounted the brace 55. The electromagnets 52 are provided under the arm holder 51. As shown in FIG. 2B, the electromagnets 52 are provided in a pair so as to face the respective disc-shaped parts 57B of the magnetic member 57. The arm holder 51 includes inclined surfaces 51A and a receiving surface 51B. The inclined surfaces 51A are arranged at positions sandwiching the electromagnets 52 from either side thereof as viewed from the surgeon. The receiving surface 51B is located above the electromagnets 52, as shown in FIG. 3B, and serves as a surface on which the fitting surfaces 57A of the brace 55 are placed. Specifically, as shown in FIG. 3B, the inclined surfaces 51A are inclined such that the fitting surfaces 57A of the brace 55 are guided to the receiving surface 51B. Hence, the inclined surfaces 51A serve as guide surfaces. Further, as shown in FIGS. 2B and 3B, a soft plastic film 61 is provided above the receiving surface 51B to reduce the sliding resistance caused between the receiving surface 51B and the fitting surfaces 57A. The soft plastic film 61 is sterilized in advance.

The surgeon places his/her arm A in the arm holder 51 so that the fitting surfaces 57A will face the receiving surface 51B. In this state, when the electromagnets 52 are excited, the end arm 5 is secured to the arm A to enable movement following the movement of the arm A in the vertical, horizontal or front-back direction, allowing the multijoint arm 3 to change its posture. When the electromagnets 52 are in an unexcited state, the surgeon can freely move his/her arm A. In particular, when the surgeon slides his/her arm A back and forth in a state where the receiving surface 51B is kept facing the fitting surfaces 57A, the soft plastic film 61 reduces the sliding resistance therebetween and hence also reduces the remnant magnetic flux that acts on the magnetic member 57.

The mode-determining computer 7 controls a drive circuit 79 connected to a power source 78 to switch excitation and non-excitation of the electromagnets 52. The computer 7 is housed in the support 41 shown in FIG. 2A. Further, as shown in FIGS. 1 and 2A, the computer 7 housed in the support 41 is connected to a foot-operated switch button 91 (mode switch button 91).

As shown in FIG. 1, the mode-determining computer 7 incorporates an electronic control circuit that includes a CPU 71, a ROM 72 and a RAM 73. When the apparatus 1 is powered on, the CPU 71 performs the following processing on the basis of a program stored in the ROM 72. Referring to the flow diagram shown in FIG. 4, hereinafter is described the processing performed by the computer 7.

Figure 4:
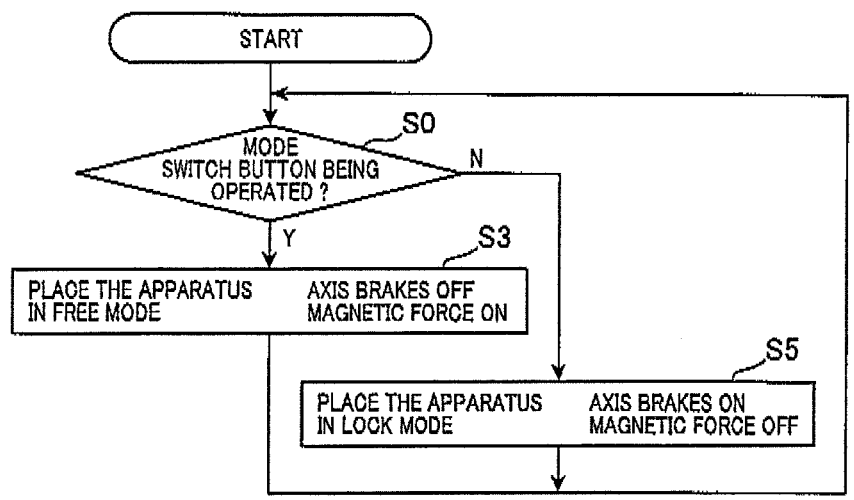
FIG. 4 is a flow diagram illustrating control in the apparatus.

As shown in FIG. 4, in this processing, at step S0, the computer 7 determines first whether or not the mode switch button 91 is being operated (i.e. whether or not it is being depressed by foot). If the mode switch button 91 is being operated (Y at step S0), control proceeds to step S3 where the operating mode is set to free mode. Then, control returns to step S0.

The free mode is provided in preparation for the surgeon's attempt to permit the end arm 5 to follow the movement (follow-up movement) of the arm A. Accordingly, in the free mode, the braking applied by the brakes 31A, 32A and 33A of the joints 31, 32 and 33, respectively, is released (hereinafter, this released state is also referred to as "axis brake(s) is/are OFF"). At the same time, in the free mode, the electromagnets 52 are excited (hereinafter, this excited state is also referred to as "magnetic force is ON"). In the free mode, the axis brakes are OFF and magnetic force is ON. Therefore, when the surgeon moves his/her arm A, the end arm 5 follows the movement of the arm A. In this case, the force applied to the arm A from the end arm 5 is quite small as mentioned above and the sliding resistance of the brakes 31A, 32A and 33A is also small. Therefore, the surgeon can permit the end arm 5 to follow the movement of his/her arm A without putting so much strength into the arm A.

On the other hand, if the switch button 91 is not being operated (N at step S0), control proceeds to step S5 where the operating mode is set to lock mode. Then, control returns to step S0. The lock mode is provided in preparation for the surgeon's attempt to lock the position of the end arm 5 and to be ready to carry out a surgery, with the arm A being located on the end arm 5. In the lock mode, braking is applied to the joints 31, 32 and 33 by the brakes 31A, 32A and 33A, respectively (axis brakes are ON), and at the same time the electromagnets 52 are unexcited (magnetic force is OFF). Since the axis brakes are ON in the lock mode, the position of the end arm 5 is steadily locked in spite of the surgeon's removal of his/her arm A from the end arm 5. However, since the joints 34 and 35 are not furnished with brakes, the angle of the end arm 5 can be freely adjusted. Further, since magnetic force is OFF, the surgeon is able to meticulously carry out the surgery without having his/her hand including the arm A been confined on the end arm 5.

Figure 5:
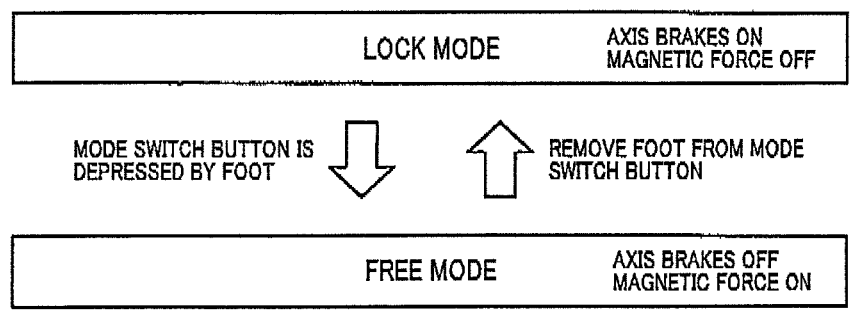
FIG. 5 is a state transition diagram illustrating transition of operating mode according to the control.

When the mode-determining computer 7 performs the foregoing processing, the operating mode of the apparatus 1 transitions as follows. FIG. 5 is a state transition diagram illustrating so transition of the operating mode. As shown in FIG. 5, when the mode switch button 91 is depressed by foot (Y at step S0), the operating mode is set to free mode throughout the period when the mode switch button 91 is depressed. In the free mode, the axis brakes are OFF and magnetic force is ON (step S3). Then, when the foot is removed from the mode switch button 91 (N at step S0), the operating mode is set to lock mode (step S5). In the lock mode, the axis brakes are ON and magnetic force is OFF.

Thus, during the work, the surgeon is able to easily place the arm A and the brace 55 on the arm holder 51 of the end arm 5 to permit the end arm 5 to follow the movement of the arm A, or easily remove the arm A and the brace 55 from the end arm 5. In this way, the surgeon can perform meticulous surgery by depressing the mode switch button 91 by foot to set the operating mode to free mode, by moving, in this state, the end arm 5 to a desired position, and by removing his/her foot from the mode switch button 91 to lock the position of the end arm 5.

Further, the soft plastic film 61 arranged between the receiving surface 51B of the arm holder 51 and the fitting surfaces 57A of the magnetic member 57 can reduce the sliding resistance that works therebetween. Specifically, since the soft film 61 having small shear strength is arranged between the hard receiving surface 51B and the hard fitting surfaces 57A, the friction coefficient between the receiving surface 51B and the fitting surfaces 57A is reduced. Therefore, when the surgeon wishes to move the arm A and the brace 55 only a little on the arm holder 51, the arm A and the brace 55 can be smoothly moved. In particular, in a microscopic surgery, in which only a slight movement of the arm A is a large movement in the surgical field, the effect of being able to minutely adjust the position the arm A is more prominently exerted.

Moreover, the soft plastic film 61, which is a non-magnetic film, forms a very small magnetic gap between each of the electromagnets 52 and the magnetic member 57. Therefore, when the electromagnets 52 are demagnetized, the remnant magnetic flux that acts on the magnetic member 57 is reduced by the soft plastic film 61 to thereby enhance the responsiveness. Owing to this, the arm A and the brace 55 can be more smoothly moved.

Such a movement of the arm A and the brace 55 on the arm holder 51 is performed in the absence of the control using actuators or sensors. Accordingly, complication in the configuration and the control of the apparatus is minimized. Further, the arm holder 51 is provided with the inclined surfaces 51A for guiding the fitting surfaces 57A of the brace 55 to the receiving surface 51B located above the electromagnets 52. Therefore, when the surgeon places his/her arm A on the arm holder 51, the fitting surfaces 57A will slide down along the inclined surfaces 51A and guided onto the receiving surface 51B, leading to more enhancement of operability.

After minutely adjusting the position of the arm A and the brace 55 in the lock mode, the operating mode is changed to free mode. Then, at the minutely adjusted position, the arm A and the brace 55 are secured to the arm holder 51. As described above, simple control is used in the present embodiment, under which the operating mode is switched in response to the operation of the mode switch button 91. The simple control can reduce the concern that erroneous operation may occur. Further, in the absence of complicated control, the size of the mode-determining computer 7 can be reduced.

Second Embodiment

Figure 6:
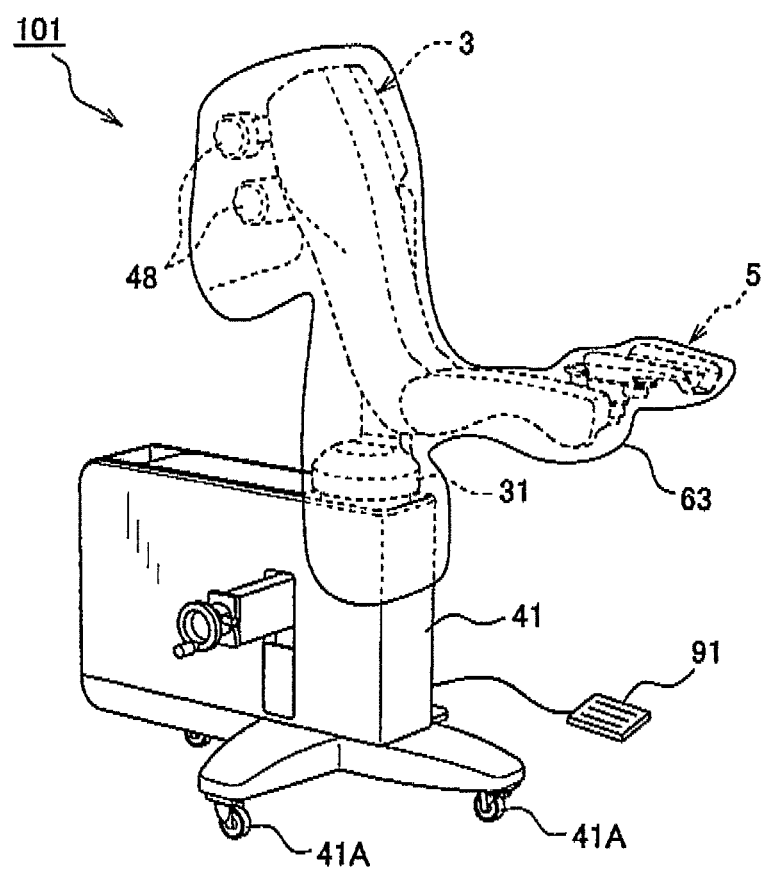
FIG. 6 is a perspective view illustrating an appearance of an apparatus for supporting and following the movement of a part of a person's body, according to a second embodiment of the present invention.

The soft plastic film may have various configurations, as provided below, other than the one described above. FIG. 6 is a perspective view illustrating an appearance of an apparatus 101 for supporting and following the movement of a part of a person's body, according to a second embodiment. As shown in FIG. 6, the soft plastic film 61 is omitted from the apparatus 101 of the second embodiment. Instead, the multijoint arm 3 and the end arm 5 as a whole are covered with a sterilized drape 63 from above. In the present embodiment, the soft plastic film 61 is not required to be particularly provided, but the conventional sterilized drape 63 is used as a soft film. Accordingly, the configuration of the apparatus is more simplified.

Third Embodiment

Figure 7:
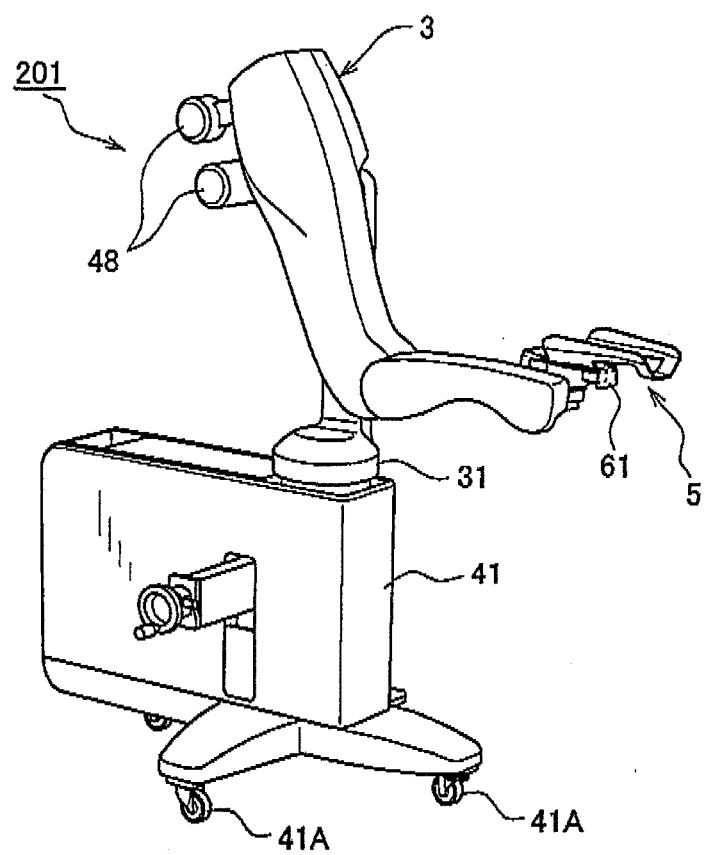
FIG. 7 is a perspective view illustrating an appearance of an apparatus for supporting and following the movement of a part of a person's body, according to a third embodiment of the present invention.
Figure 8:
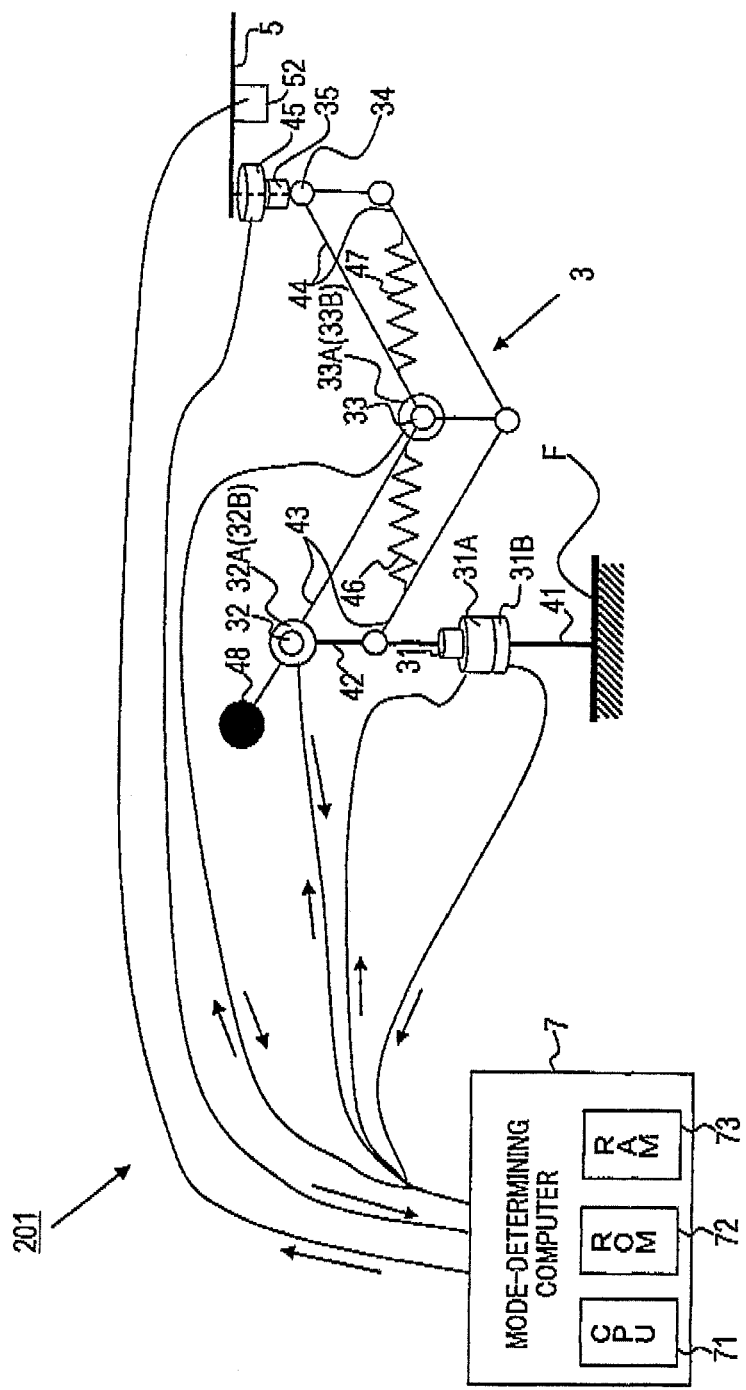
FIG. 8 is a schematic view illustrating a configuration of the apparatus.

Referring to FIGS. 7 to 10, a third embodiment of the present invention is described. FIG. 7 is a perspective view illustrating an appearance of an apparatus 201 for supporting and following the movement of a part of a person's body, according to the third embodiment. As shown in FIG. 7, the mode switch button 91 may be omitted from the apparatus 201. In the third embodiment, as schematically illustrated in FIG. 8, the apparatus 201 includes the following sensors so that the mode-determining computer 7 can automatically switch the operating mode of the apparatus 201 on the basis of the detection signals acquired from the sensors. Specifically, as shown in FIG. 8, the joint 31 is provided with an encoder 31B that detects the amount of rotation of the shoulder 42 with respect to the support 41. Similar to the joint 31, the joints 32 and 33 are also provided with encoders 32B and 33B, respectively. The end arm 5 is connected to the joint 35 via a force sensor 45. The force sensor 45 detects three axial forces applied to the end arm 5 and the torque around three axes.

Figure 9:
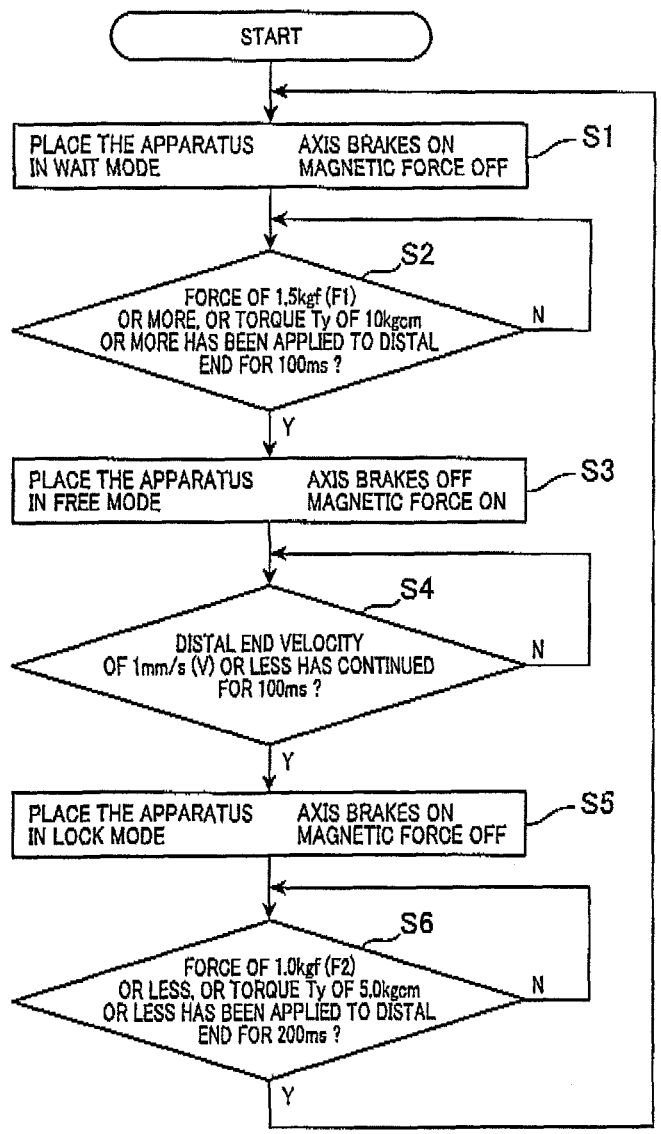
FIG. 9 is a flow diagram illustrating control in the apparatus.

The mode-determining computer 7 carries out the processing shown in FIG. 9 on the basis of the detection signals acquired from the sensors to thereby switch the operating mode as set forth below. As shown in FIG. 9, the computer 7 firstly sets, at step S1, the operating mode to wait mode. The wait mode is provided in preparation for a situation in which the arm A is absent from the end arm 5. Specifically, in the wait mode, braking is applied to the joints 31, 32 and 33 by the brakes 31A, 32A and 33A, respectively (axis brakes are ON), while the electromagnets 52 are unexcited (magnetic force is OFF). Since magnetic force is OFF in the wait mode, the surgeon can easily place his/her arm A on the end arm 5 or easily remove his/her arm A from the end arm 5. Further, since the axis brakes are ON, the position of the end arm 5 is steadily locked when the surgeon removes his/her arm A from the end arm 5.

At the subsequent step S2, the computer 7 makes a determination as set forth below on the basis of a detection signal acquired from the force sensor 45 to determine whether or not the surgeon is attempting to permit the end arm 5 to follow the movement of his/her arm A (follow-up movement).

When attempting to positively permit the end arm 5 to follow the movement of the arm A, the surgeon will firstly support his/her arm A with his/her muscle (first stage) and then apply a force to the end arm 5 via his/her arm A (second stage). In the description of the present step, the threshold of the force applied to the end arm 5 at the first stage is F2, and the threshold of the force applied to the end arm 5 at the second stage is F1. Specifically, when the surgeon attempts to permit the end arm 5 to follow the movement of the arm A, the arm A is supported by the muscle of his/her own and hence the force applied to the end arm 5 from above will be not more than F2 (e.g., 1.0 kgf). Then, when the surgeon positively applies a force to the end arm 5 via the arm A to cause the follow-up movement in the end arm 5, the end arm 5 is applied with a force of not less than F1 (e.g., 1.5 kgf that is a rough standard of the dead weight of the arm A in the follow-up movement in the downward direction: the present processing is described on the basis of this numerical value). The values of F1 and F2 set in advance in the present processing may desirably satisfy a relation: Dead weight of arm A≥F1>F2.

Thus, at step S2, the computer 7 determines whether or not there has been a duration of 100 ms in a state where the force applied to the end arm 5 (distal end) becomes equal to or larger than 1.5 kgf (F1), or the torque (Ty) applied to the end arm 5 becomes equal to or larger than 10 kgcm that corresponds to F1. Similar to the numerical value of F1, the numerical value of the torque or the duration is provided as an example in the present processing and thus may be variously changed (the same applies to other numerical values). If the above state has not continued for 100 ms (N at step S2), control stands by at step S2. Thus, the operating mode is retained to be the wait mode that has been set at step S1. On the other hand, when the above state has continued for 100 ms (Y at step S2), it means that the surgeon is attempting to cause the follow-up movement of the end arm 5. In this case, control proceeds to step S3 where the operating mode is set to free mode, similar to the first embodiment.

Then, at step S4, the computer 7 determines whether or not the surgeon has finished moving the arm A and is attempting to lock the end arm 5 at the position. This determination is made on the basis of whether or not there has been a duration of 100 ms in a state where the end arm 5 (distal end) moves at a velocity of 1 mm/s or less. The velocity of the end arm 5 is detected via the encoders 31B, 32B and 33B. If the above state has not continued for 100 ms (N at step S4), control stands by at step S4. Thus, the operating mode is retained to be the free mode that has been set at step S3. On the other hand, if the above state has continued for 100 ms (Y at step S4), control proceeds to step S5 where the operating mode is set to lock mode, similar to the first embodiment.

At the subsequent step S6, the computer 7 determines whether or not there has been a duration of 200 ms in a state where the force applied to the end arm 5 (distal end) is 1.0 kgf (F2) or less, or the torque applied to the end arm 5 is 5.0 kgcm, which corresponds to F2, or less. If the above state has not continued for 200 ms (N at step S6), control stands by at step S6 to retain the operating mode to be so the lock mode that has been set at step S5. On the other hand, if the above state has continued for 200 ms (Y at step S6), control returns to step S1 described above to set the operating mode to wait mode.

As mentioned above, the state where the force applied to the end arm 5 is F2 or less means that the surgeon has supported his/her arm A with his/her own muscle attempting to move his/her arm A. However, the similar state will also be created when the surgeon is attempting to remove his/her arm A from the end arm 5. In the former case, an affirmative determination will be immediately made at the subsequent step S2 and then control will proceed to step S3. However, in the latter case, a negative determination will be made successively at step S2 and thus the operating mode is retained to be the wait mode that has been set at step S1.

Figure 10:
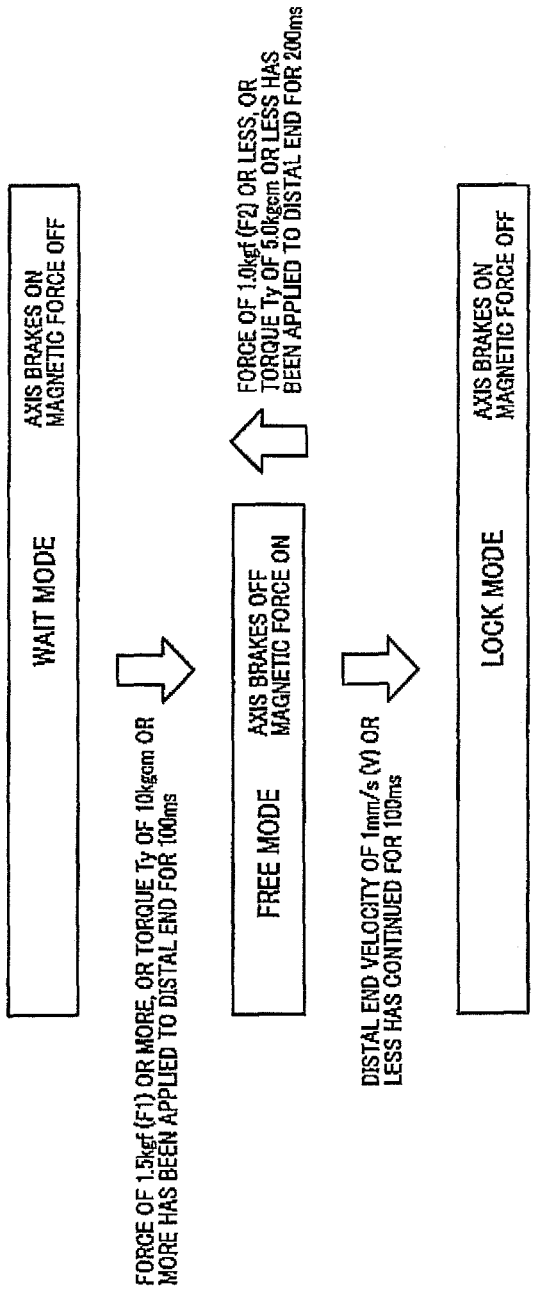
FIG. 10 is a state transition diagram illustrating transition of operating mode according to the control.

When the computer 7 performs the series of steps described above, the operating mode of the apparatus 1 transitions as follows. Specifically, as shown in FIG. 10, while the operating mode is set to wait mode (step S1), the axis brakes are ON and magnetic force is OFF. While the operating mode is set to wait mode, if there has been a duration of 100 ms in a state where the force applied to the end arm 5 (distal end) is 1.5 kgf (F1) or more, or the torque applied to the end arm 5 is 10 kgcm or more (Y at step S2), the operating mode is set to free mode (step S3).

While the operating mode is set to free mode, if there has been a duration of 100 ms in a state where the velocity of the end arm 5 (distal end) is 1 mm/s or less (Y at step S4), the operating mode is set to lock mode (step S5). While the operating mode is set to lock mode, if there has been a duration of 200 ms in a state where the force applied to the end arm 5 (distal end) is 1.0 kgf (F2) or less, or the torque applied to the end arm 5 is 5.0 kgcm or less (Y at step S6), the operating mode is set to wait mode (step S1).

As described above, in the present embodiment, the operating so mode can be switched in a sequence of wait mode, free mode, lock mode, and to wait mode, according to the condition of the strength put into the arm A by the surgeon and the duration of the condition. Therefore, there is no need to operate switches or the like in order to switch the operating mode. Accordingly, the surgeon is able to smoothly perform the surgery. Moreover, since the three modes are sequentially and unidirectionally switched, the surgeon will easily and instinctively know the operating mode in which the apparatus is operating, thereby reducing erroneous operation of the apparatus. Further, in the present embodiment, the end arm 5 is permitted to follow the movement of the arm A even when not so much a strength is put into the arm A, as mentioned above. In addition, since the arm A can be easily placed on and removed from the end arm 5, remarkably good operability is achieved.

Fourth Embodiment

Figure 11:
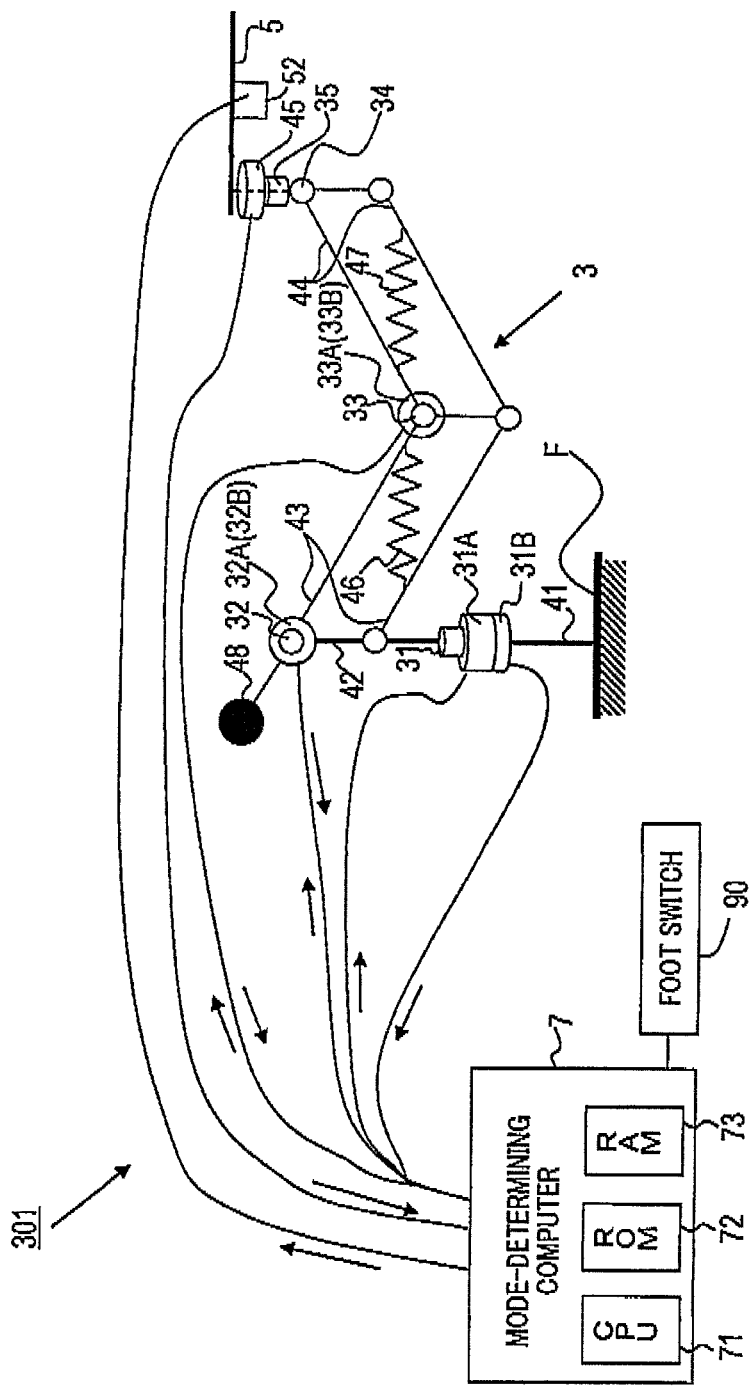
FIG. 11 is a schematic view illustrating an apparatus for supporting and following the movement of a part of a person's body, according to a fourth embodiment to which the present invention is applied.
Figure 12:
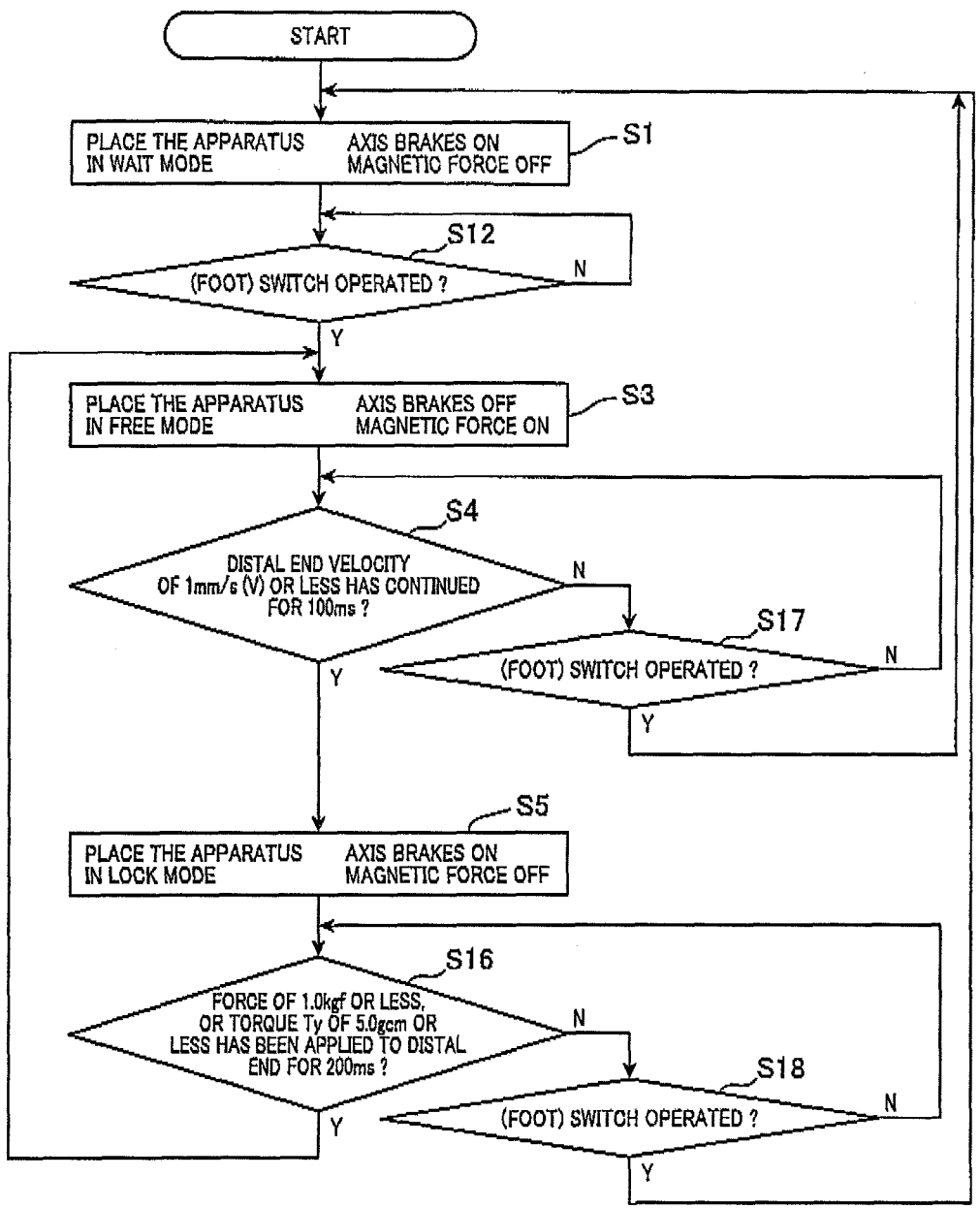
FIG. 12 is a flow diagram illustrating control in the apparatus.

The way of switching the operating mode may further be variously changed as follows. FIG. 11 is a schematic view illustrating an apparatus 301 for supporting and following the movement of a part of a person's body, according to a fourth embodiment of the present invention. The apparatus 301 shown in FIG. 11 is different in the configuration from the first embodiment in that a foot switch 90 is connected to the mode-determining computer 7. Accordingly, the processing performed by the computer 7 is as shown in FIG. 12. In the present embodiment, the foot switch 90 may be replaced by a different switch.

As shown in FIG. 12, similar to the third embodiment, at step S1, the operating mode is set to wait mode. After that, at step S12, the computer 7 determines whether or not the foot switch 90 has been operated. If the foot switch 90 has not been operated (N at step S12), control stands by at step S12 to retain the operating mode to be the wait mode that has been set at step S1. On the other hand, if the foot switch 90 has been operated (Y at step S12), control proceeds to step S3 where the operating mode is set to free mode, similar to the first embodiment.

After the operating mode is set to free mode, if there has been a duration of 100 ms in a state where the velocity of the end arm 5 (distal end) is 1 mm/s or less (Y at step S4), control proceeds to step S5 where the operating mode is set to lock mode, similar to the third embodiment. However, in the present embodiment, if the above state has not continued for 100 ms (N at step S4), control proceeds to step S17 where the computer 7 determines whether or not the foot switch 90 has been operated. If the foot switch 90 has not been operated (N at step S17), control returns to step S4. In the processing loop of steps S4 and S17, the operating mode is retained to be free mode. However, if the foot switch 90 is operated (Y at step S17) before the above state is continued for 100 ms (N at step S4), control returns to step S1 where the operating mode is set to wait mode.

On the other hand, when the operating mode is set to lock mode at step S5, the computer 7 determines, at the subsequent step S16, whether or not there has been a duration of 200 ms in a state where the force applied to the end arm 5 (distal end) is 1.0 kgf or less, or the torque applied to the end arm 5 is 5.0 kgcm or less, similar to step S6 described above. If the above state has continued for 200 ms (Y at step S16), control returns to step S3 where the operating mode is set to free mode.

Specifically, as mentioned above, the state where the force applied to the end arm 5 is 1.0 kgf or less means that the surgeon has supported his/her arm A with his/her own muscle attempting to move his/her arm A. Accordingly, in the present embodiment, if such a state continues, the operating mode is set to free mode. On the other hand, if the above state has not continued for 200 ms (N at step S16), control proceeds to step S18 where the computer 7 determines whether or not the foot switch 90 has been operated. If the foot switch 90 has not been operated (N at step S18), control returns to step S16. In the processing loop of steps S16 and S18, the operating mode is retained to be lock mode. However, if the foot switch 90 is operated (Y at step S18) before the above state continues for 200 ms (N at step S16), control returns to step S1 where the operating mode is set to wait mode.

Figure 13:
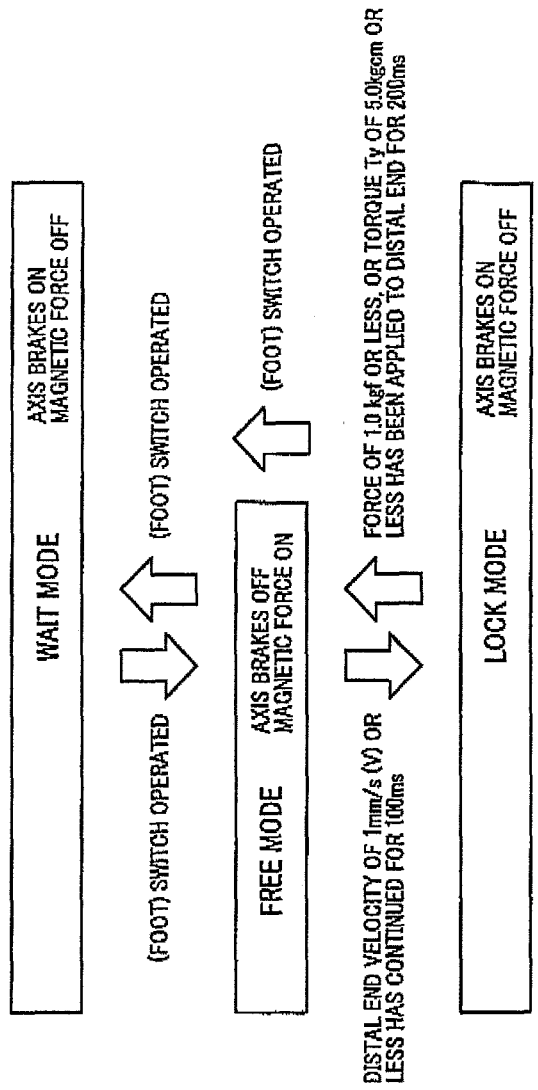
FIG. 13 is a state transition diagram illustrating transition of operating mode according to the control.

The series of steps set forth above is performed by the computer 7 to transition the operating mode of the apparatus 301 as follows. Specifically, as shown in FIG. 13, when the foot switch 90 is operated (Y at step S12) while the operating mode is set to wait mode, the operating mode will be set to free mode (step S3). Further, when the foot switch 90 is operated (Y at step S17 or Y at step S18) while the operating mode is set to free mode or lock mode, the operating mode will be set to wait mode.

Also, while the operating mode is set to free mode, if there has been a duration of 100 ms in a state where the velocity of the end arm 5 (distal end) is 1 mm/s or less (Y at step S4), the operating mode will be set to lock mode (step S5). While the operating mode is set to lock mode, if there has been a duration of 200 ms in a state where the force applied to the end arm 5 (distal end) is 1.0 kgf or less, or the torque applied to the end arm 5 is 5.0 kgcm or less, the operating mode will be set to free mode (step S3).

As described above, in the present embodiment, the operating mode is automatically switched between free mode and lock mode, according to the condition of the strength put into the arm A by the surgeon and the duration of the condition. Thus, the surgeon is able to smoothly perform the surgery.

In addition, the state where the operating mode is mutually switchable between free mode and lock mode can be switched to wait mode, or vice versa, by operating the foot switch 90. Thus, the switchable state can be reliably switched to wait mode by operating the foot switch 90 in a scene where the end arm 5 is not desired to follow the movement of the arm A, such as when the surgeon takes a surgical tool, or a scene where the end arm 5 is absolutely not desired to be moved in the case where the surgeon carries out a particularly important work. Moreover, since the operating mode is reliably retained to wait mode until the next time the foot switch 90 is operated, the surgeon is able to carry out the surgery with a sense of ease. In the present embodiment, when the foot switch 90 is operated while the operating mode is set to wait mode, the operating mode may be set to lock mode.

Fifth Embodiment

Figure 14:
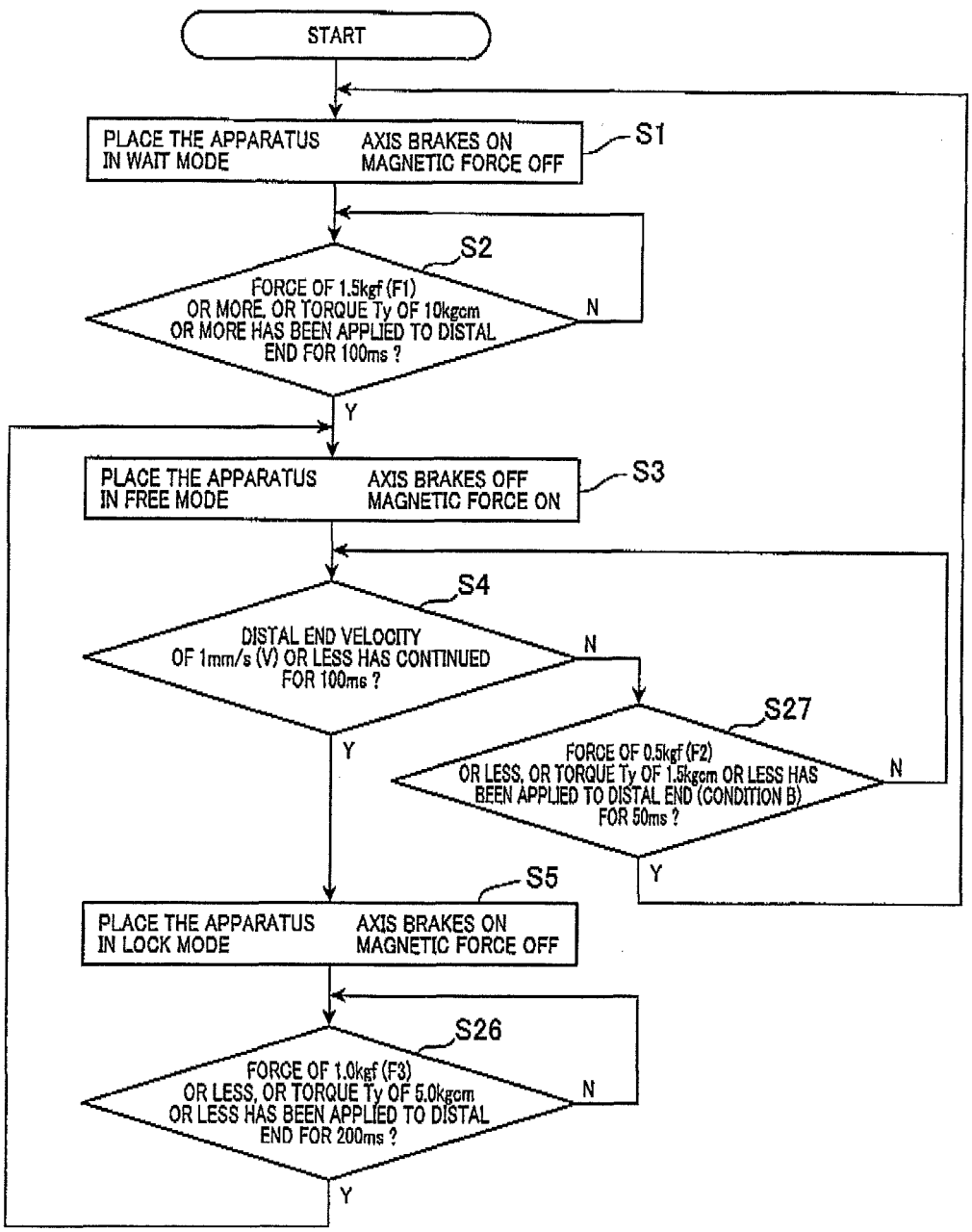
FIG. 14 is a flow diagram illustrating control of an apparatus for supporting and following the movement of a part of a person's body, according to a fifth embodiment to which the present invention is applied.

Referring to FIGS. 14 and 15, hereinafter is described a fifth embodiment to which the present invention is applied. The present embodiment is different from the third embodiment in that the series of steps performed by the computer 7 in the apparatus 1, which is configured similar to the third embodiment, has been changed as shown in FIG. 14.

In the present embodiment, reference F3 indicates the threshold of a force applied to the end arm 5, the threshold being used for determining that the surgeon has supported his/her arm A with his/her own muscle. Reference F2 indicates the threshold of a force applied to the end arm 5, the threshold being used for determining that the surgeon has not placed his/her arm A on the end arm 5. Further, reference F1 indicates the threshold of a force applied to the end arm 5, the threshold being used for determining that the surgeon has attempted to permit the end arm 5 to follow the movement of the arm A. References F1, F2 and F3 may desirably satisfy a relation: Dead weight of arm A≥F1>F3>F2>0. For example, F1=1.5 kgf, F2=0.5 kgf and F3=1.0 kgf.

FIG. 14 is a flow diagram illustrating control performed by the apparatus 1 for supporting and following the movement of a part of a person's body, according to the fifth embodiment. In the series of steps shown in FIG. 14, the sequential steps of S1→S2→S3→S4→S5 are similar to those of the third embodiment. However, after the operating mode has been set to free mode (step S3), if there has not been a duration of 100 ms in a state where the velocity of the end arm 5 is 1 mm/s or less (hereinafter referred to as state A) (N at step S4), control proceeds to step S27. At step 27, the computer 7 determines whether or not the arm A is placed on the end arm 5, as follows.

Specifically, at step S27, the computer 7 determines whether or not there has been a duration of 50 ms in a state where the force applied to the end arm 5 (distal end) is 0.5 kgf (F2) or less, or the torque (Ty) applied to the end arm 5 is 1.5 kgcm, which corresponds to F2, or less (hereinafter referred to as state B). If the state B has not continued for 50 ms (N at step S27), control returns to step S4. In the processing loop of steps S4 and S27, the operating mode is retained to be free mode. If the state B has continued for 50 ms at step S27) before the state A continues for 100 ms (N at step S4), control returns to step S1 where the operating mode is set to wait mode.

On the other hand, when the operating mode is set to lock mode at step S5, control proceeds to step S26. At step S26, similar to step S6 described above, the computer 7 determines whether or not there has been a duration of 200 ms in a state where the force applied to the end arm 5 (distal end) is 1.0 kgf (F3) or less, or the torque (Ty) applied to the end arm 5 is 5.0 kgcm, which corresponds to F3, or less. If the above state has continued for 200 ms (Y at step S26), control returns to step S3 described above, where the operating mode is set to free mode. In the present embodiment as well, similar to the fourth embodiment, the state where the force applied to the end arm 5 is 1.0 kgf or less means that the surgeon has supported his/her arm A with his/her own muscle attempting to so move the arm A. Accordingly, when such a state continues, the operating mode is set to free mode. On the other hand, if the above state has not continued for 200 ms (N at step S26), control stands by at step S26, retaining the operating mode to be the lock mode that has been set at step S5.

The computer 7 carries out the series of steps described above to allow the operating mode of the apparatus 301 to transition as follows. Specifically, as shown in FIG. 15, while the operating mode is set to wait mode, if there has been a duration of 100 ms in a state where the force applied to the end arm 5 (distal end) is 1.5 kgf (F1) or more, or the torque applied to the end arm 5 is 5 kgcm or more (Y at step S2), the operating mode will be set to free mode (step S3). While the operating mode is set to free mode, if there has been a duration of 100 ms in a state where the velocity of the end arm (distal end) is 1 mm/s or less (Y at step S4), the operating mode will be set to lock mode (step S5).

Further, while the operating mode is set to lock mode, if there has been a duration of 200 ms in a state where the force applied to the end arm 5 (distal end) is 1.0 kgf or less, or the torque applied to the end arm 5 is 5.0 kgcm or less (V at step S26), the operating mode will be set to free mode (step S3). Furthermore, while the operating mode se set to free mode, if there has been a duration of 50 ms in a state where the force applied to the end arm 5 (distal end) is 0.5 kgf (F2) or less, or the torque applied to the end arm 5 is 1.5 kgcm or less (Y at step S27), the operating mode will be set to wait mode (step S1).

As described above, in the present embodiment, the operating mode can be automatically and sequentially switched between weight mode, free mode and lock mode, according to the condition of the strength put into the arm A by the surgeon and the duration of the condition. Accordingly, the surgeon is able to smoothly carry out the surgery.

In addition, the switching according such as to the condition of the strength put into the arm A enables switching from lock mode to free mode. Therefore, the surgeon can move the end arm 5 more perceptively and spontaneously. Also, the switching according such as to the condition of the strength put into the arm A also enables switching from free mode to wait mode. Therefore, the surgeon is able to change surgical tools, for example, more spontaneously and promptly.

In the foregoing embodiments, the arm A corresponds to a part of a person's body. Similarly, the end arm 5, which functions as an armrest described above in the embodiment, corresponds to the load device; the multijoint arm 3 corresponds to the support; the electromagnets 52 correspond to the securing member; the soft plastic film 61 or the sterilized drape 63 corresponds to the film; the spring 46 or 47, or the counter weight 48 corresponds to the balancing mechanism; the brake 31A, 32A or 33A corresponds to the brake; the encoder 31B, 32B or 33B, or the force sensor 45 corresponds to the detector; the mode switch button 91 or the foot switch 90 corresponds to the switch; and the mode-determining computer 7 corresponds to the determining means or the switching means. In the series of steps performed by the computer 7, steps S1, S3 and S5 correspond to the switching means; and steps S2, S4, S6, S16, S26 and S27 correspond to the determining means.

The present invention is not limited to the foregoing embodiments but may be implemented in various modes within a scope not departing from the spirit of the present invention.

For example, the support may support the load device so as to be only unidirectionally movable. Further, each fitting surface and the receiving surface do not necessarily have to be mutually flat but may be mutually curved. In addition, the soft film does not necessarily have to be made of plastic, but other various films, such as fabric, may be used for forming the soft film. The securing member described above is configured such that the magnetic member 57 is attracted to the electromagnets 52. Other than this, various modes may be available for the securing member, such as a mode using static electricity or suction of air. In the foregoing embodiments, whether the surgeon is attempting to move his/her arm A is determined by detecting the force or the torque. Alternative to this, the surgeon's attempt of moving his/her arm A may be determined by detecting the position, velocity or acceleration of the end arm 5 or by detecting the state of contact between the end arm 5 and the arm A.

What is claimed is:

1. An apparatus for supporting a part of a person's body, the apparatus comprising:
    a brace to be mounted on a part of a person's body, the brace having a hard fitting surface;
    a load device provided with a hard receiving surface to receive the fitting surface of the brace;
    a support provided with at least one flexible joint and configured to movably support the load device by flexing the joint;
    a securing member provided at the load device and configured to secure the receiving surface to the fitting surface and to enable the load device to move and follow movement of the part of the person's body and the brace against resistance applied from the support;
    a brake configured to limit the movement of the load device by suppressing flex motions of the joint of the support;
    switching means for switching an operation mode of the apparatus, at least, to a free mode or to a limiting mode, wherein the free mode is an operating mode in which the securing member and the brake are controlled to secure the brace to the load device by the securing member and the load device is released from being limited in movement by the brake, and the limiting mode is another operating mode in which the brace is released from being secured by the securing member and the brake limits the movement of the load device; and a soft film arranged between the receiving surface and the fitting surface.

2. The apparatus of claim 1, wherein the load device comprises a guide surface configured to guide the fitting surface of the brace toward the receiving surface.

3. The apparatus of claim 2, wherein the guide surface is composed of inclined surfaces positioned on both lateral sides of the securing member and formed to becomes narrower in width as approaching the securing member.

4. The apparatus of claim 2, wherein
the securing member comprises an electromagnet;
the brace has a magnetic member attached to the fitting surface hereof; and
the film is nonmagnetic.

5. The apparatus of claim 4, wherein the film is sterilized.

6. The apparatus of claim 5, wherein a balancing mechanism that supports the load device against weight directly or indirectly applied to the load device, the directly or indirectly applied weight to the load device being any of a dead weight of the load device, a dead weight of the securing member, a dead weight of the brace, and a dead weight of the part of the person's body,
wherein the balancing mechanism is configured to achieve a balance with any of forces directly or indirectly applied to the load device, the support, and the securing member by directly or indirectly apply a force to the load device, the support, or the securing member.

7. The apparatus of claim 6, comprising a switch to be manipulated by other parts of the person's body,
wherein the switching means is configured to switch the operating mode depending on manipulated states of the switch.

8. The apparatus of claim 7, comprising:
a detector that detects at least any one of physical quantities including i) a force applied from the part of the person's body and the brace to the load device or the securing member, ii) a torque applied from the part of the person's body and the brace to the load device or the securing member, iii) an acceleration of either the load device or the securing member, iv) a velocity of either the load device or the securing member, v) a position of the load device or the securing member, and vi) a contact between the load device or the securing member and the part of the person's body or the brace; and
determining member for determining, based on a result detected by the detector, whether or not the part of the person's body is about to move either the load device or the securing member,
wherein the switching means is configured to switch the operating mode such that, when the determining means determine that the part of the person's body is about to move either the load device or the securing member, the operating mode is switched to the free mode, and when the determining means determine that the part of the person's body is not about to move either the load device or the securing member, the operating mode is switched to the limiting mode.

9. The apparatus of claim 8, wherein the part of the person's body is an arm of the person and the brace is configured to be wound around the arm.

10. The apparatus of claim 4, wherein
the support is covered with a sterilized drape, and
a part of the sterilized drape is configured to serve as the film.

11. The apparatus of claim 2, wherein the film is sterilized.

12. The apparatus of claim 11, wherein a balancing mechanism that supports the load device against weight directly or indirectly applied to the load device, the directly or indirectly applied weight to the load device being any of a dead weight of the load device, a dead weight of the securing member, a dead weight of the brace, and a dead weight of the part of the person's body,
wherein the balancing mechanism is configured to achieve a balance with any of forces directly or indirectly applied to the load device, the support, and the securing member by directly or indirectly apply a force to the load device, the support, or the securing member.

13. The apparatus of claim 12, comprising:
a detector that detects at least any One of physical quantities including i) a force applied from the part of the person's body and the brace to the load device or the securing member, ii) a torque applied from the part of the person's body and the brace to the load device or the securing member, iii) an acceleration of either the load device or the securing member, iv) a velocity of either the load device or the securing member, v) a position of the load device or the securing member, and vi) a contact between the load device or the securing member and the part of the person's body or the brace; and
determining member for determining, based on a result detected by the detector, whether or not the part of the person's body is about to move either the load device or the securing member,
wherein the switching means is configured to switch the operating mode such that, when the determining means determine that, the part of the body is about to move either the load device or the securing member, the operating mode is switched to the free mode, and when the determining means determine that the part of the person's body is not about to move either the load device or the securing member, the operating mode is switched to the limiting mode.

14. The apparatus of claim 1, wherein
the securing member comprises an electromagnet;
the brace has a magnetic member attached to the fitting surface hereof; and
the film is nonmagnetic.

15. The apparatus of claim 14, wherein
the support is covered with a sterilized drape, and
a part of the sterilized drape is configured to serve as the film.

16. The apparatus of claim 1, wherein the film is sterilized.

17. The apparatus of claim 1, wherein a balancing mechanism that supports the load device against weight directly or indirectly applied to the load device, the directly or indirectly applied weight to the load device being any of a dead weight of the load device, a dead weight of the securing member, a dead weight of the brace, and a dead weight of the part of the person's body,
wherein the balancing mechanism is configured to achieve a balance with any of forces directly or indirectly applied to the load device, the support, and the securing member by directly or indirectly apply a force to the load device, the support, or the securing member.

18. The apparatus of claim 17, comprising:
a detector that detects at least any one of physical quantities including i) a force applied from the part of the person's body and the brace to the load device or the securing member, ii) a torque applied from the part of the person's body and the brace to the load device or the securing member, iii) an acceleration of either the load device or the securing member, iv) a velocity of either the load device or the securing member, v) a position of the load device or the securing member, and vi) a contact between the load device or the securing member and the part of the person's body or the brace; and determining member for determining, based on a result detected by the detector, whether or not the part of the person's body is about to move either the load device or the securing member, wherein the switching means is configured to switch the operating mode such that, when the determining means determine that the part of the person's body is about to move either the load device or the securing member, the operating mode is switched to the free mode, and when the determining means determine that the part of the person's body is not about to move either the load device or the securing member, the operating mode is switched to the limiting mode.

19. The apparatus of claim 1, comprising a switch to be manipulated by other parts of the person's body,
wherein the switching means is configured to switch the operating mode depending on manipulated states of the switch.

20. The apparatus of claim 1, wherein the part of the person's body is an arm of the person and the brace is configured to be wound around the arm.

* * * * *